United States Patent [19]

Vlodavsky et al.

[11] Patent Number: 5,206,223
[45] Date of Patent: Apr. 27, 1993

[54] METHOD FOR INHIBITING HEPARANASE ACTIVITY

[75] Inventors: Israel Vlodavsky; Amiram Eldor; Yaakov Naparstek, all of Jerusalem; Irun Cohen, Rehovet, all of Israel

[73] Assignee: Yeda Research and Development Co. Ltd., Rehovot, Israel

[21] Appl. No.: 583,851

[22] Filed: Sep. 17, 1990

Related U.S. Application Data

[63] Continuation-in-part of Ser. No. 418,710, Oct. 3, 1989, abandoned, which is a continuation of Ser. No. 67,583, Jun. 24, 1987, abandoned.

[30] Foreign Application Priority Data

Jun. 26, 1986 [IL] Israel ..................................... 79254

[51] Int. Cl.$^5$ ................... A61K 31/725; C08B 37/10
[52] U.S. Cl. ..................................... 514/56; 514/825; 514/885; 536/21
[58] Field of Search ................... 514/56, 825, 885; 536/21

[56] References Cited

U.S. PATENT DOCUMENTS

| | | | |
|---|---|---|---|
| 3,033,750 | 5/1962 | Velluz et al. | 536/21 |
| 3,062,716 | 11/1962 | Montandraud | 514/56 |
| 3,636,202 | 1/1972 | Klein | 514/56 |
| 4,882,318 | 11/1989 | Vlodavsky et al. | 514/56 |
| 4,889,808 | 12/1989 | Rappaport | 514/56 |

FOREIGN PATENT DOCUMENTS

114589 8/1984 European Pat. Off. ............ 514/56

OTHER PUBLICATIONS

Folkman et al., Science, vol. 221, 19 Aug. 1983, pp. 719-725.
MacDonald, Chem. Abstracts, vol. 72:76999g (1970).

*Primary Examiner*—Jacqueline Stone
*Attorney, Agent, or Firm*—Browdy and Neimark

[57] ABSTRACT

Heparanase activity in a patient may be inhibited by administering an effective heparanase-inhibiting amount of heparin or an effective chemically modified derivative of heparin which inhibits heparanase activity. Such derivatives are preferably N-desulfated, N-acetylated heparin or O-desulfated, N-acetylated heparin. By means of this invention, allograft rejection may be prevented or delayed and autoimmune diseases such as arthritis may be alleviated and treated.

9 Claims, 6 Drawing Sheets

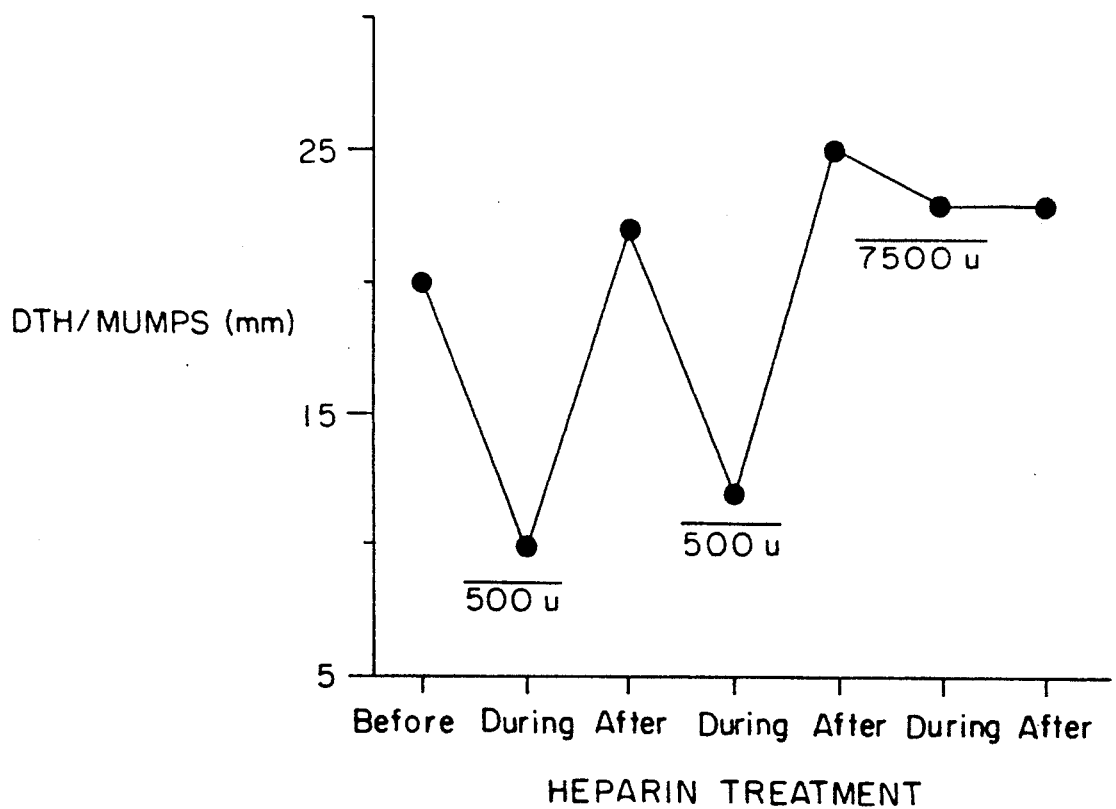

METHOD FOR INHIBITING HEPARANASE ACTIVITY

CROSS-REFERENCE WITH RELATED APPLICATIONS

This application is for a continuation-in-part application of U.S. Ser. No. 07/418,710 filed on Oct. 3, 1989, now abandoned, which is a continuation application of U.S. Ser. No. 07/067,583 filed on Jun. 24, 1987, now abandoned, the entire contents of both of which are hereby incorporated by reference.

FIELD OF THE INVENTION

The invention relates to pharmaceutical compositions and to a method for delaying or preventing the rejection of allografts and for alleviating and treating autoimmune diseases in mammals, comprising administering a low dosage of heparin or of a chemically modified derivative thereof.

BACKGROUND OF THE INVENTION

Along with its vital role in protecting the individual against foreign invaders, the immune system may attack the individual's own tissues, thereby producing autoimmune diseases. Another undesirable activity of the immune system is the rejection of critical transplanted organs. The ability of the immune system to produce autoimmune disease or reject allografts depends on the ability of lymphocytes, particularly activated T lymphocytes, to enter the target organ or grafted tissue. Traffic to the target is by way of blood vessels and the activated T lymphocytes must be able to enter and exit through the vessel walls. Therefore, it is reasonable to suppose that the participation of T lymphocytes in autoimmune damage or graft rejection might be prevented by measures affecting their traffic.

It was discovered recently by us that T lymphocytes expressed a heparanase enzyme that specifically attacked the glycosaminoglycan moiety of the extracellular matrix secreted by endothelial cells that line blood vessels (Naparstek, Y., Cohen, I. R., Fuks, Z., and I. Vlodavsky. Activated T lymphocytes produce a matrix-degrading heparan sulphate endoglycosidase, Nature 310: 241-243 (1984)). The presence of this enzyme was associated with the ability of autoimmune T lymphocytes to penetrate blood vessel walls and to attack the brain in a model disease called experimental autoimmune encephalomyelitis (EAE).

Furthermore, it was found that the heparanase enzyme could be inhibited by heparin and by some modified heparin molecules, such as N-desulfated, N-acetylated heparin, but not by others such as totally desulfated heparin (Table 1).

In U.S. Pat. No. 4,882,318, commonly assigned to the same assignees, a method for decreasing tumor metastasis in a mammal is disclosed, comprising the administration to a mammal having a malignant tumor of about 0.05 mg/kg/day to 0.5 mg/kg/day of intact heparin or of N-desulfated, N-acetylated heparin.

Intact heparin at anticoagulant doses was used to modify the course of EAE in guinea-pigs, but was not considered a useful treatment of disease because of the danger of hemorrhage (Chelmicka-Szorc, E., Arnason, B. G. W., Arch.Neural. 27:153 (1972)). A heparin devoid of anticoagulant activity (prepared by filtration through an antithrombin column), was used to inhibit delayed type hypersensitivity reactions to foreign antigens (Schneeberger, M. S. Sr., McCluskey, R., Greene, M. I., Rosenberg, R. D., Benacerraf, B., Cell.Immunol. 82:23 (1983)). Intact heparin at doses of 17-35 mg/kg/rat was shown to inhibit the emigration of lymphocytes from the circulation (Bradfield, J. W. B., Born, G. V. R., Nature 222:1183 (1969)). Intact heparin administered with cortisone was shown to inhibit angiogenesis and cause regression of tumors (Folkman, J., Langer, R. Lindhardt, R. J., Mandelschild, C., Taylor, S., Science 221:719 (1983)).

Compositions describing heparin together with other active ingredients are described in the literature. U.S. Pat. No. 3,636,202 (Klein) discloses the sequential administration of two compositions, wherein the first contains a combination of histamine, serotonin and heparin, and where the second contains oxytetracycline, lincomycin, and nicotinic acid. None of the five ingredients used in addition to heparin are part of the present invention.

European Patent Application EP 0114589 (Folkman et al.) describes a composition for inhibition of angiogenesis in mammals in which the active agents consist essentially of 1) heparin or a heparin fragment which is a hexasaccharide or larger, and 2) cortisone or hydrocortisone or the 11-α isomer of hydrocortisone. According to the disclosure, heparin by itself or cortisone by itself are ineffective: only the combination of both gives the desired effects. Furthermore, there is no proof in the literature that there is a connection between angiogenesis and autoimmune diseases. Folkman, on page 5 of the patent application, connects angiogenesis with psoriasis and with arthritis indicating the use of doses of 25,000 units to 47,000 units per day, i.e. about 600 units per kg patient weight×70 kg, while according to the present invention heparin is used alone and the total dosage is, at its upper level, 500 units/day.

U.S. Pat. No. 3,033,750 (Velluz et al.) describes the preparation of N-desulfated optionally N-acetylated heparins devoid of high anti-coagulant activity.

Horvath, J. E. et al., (1975) Low Dose Heparin and Early Kidney Transplant Function, Aust. N. Z. J. Med. Vol 5, No. 6, pp. 537-539 describe the effect of subanticoagulant doses of subcutaneous heparin on early renal allograft function. The daily dosage is high (5000 U) and the conclusion of the study is that heparin in subanticoagulant doses has no effect on early graft function or graft survival and that it may be associated with increased hemorrhagic complications.

Toivonen, M. L. et al., (1982) Rat adjuvant arthritis as a model to test potential antirheumatic agents, Meth. and Find. Exptl. Clin. Pharmacol., Vol 4, No. 6, pp. 359-363, examined the effect of heparin in high dosage (1000 U/rat) in inhibition of adjuvant arthritis in rats and found that heparin enhanced the severity of the rat adjuvant arthritis.

The use of intact heparin by itself or of some chemically modified derivatives thereof in low, subanticoagulant doses, has not been disclosed in the literature for the purposes of the present invention and some of the references teach away from the invention.

SUMMARY OF THE INVENTION

According to the invention, there are provided pharmaceutical compositions for delaying or preventing the rejection of allografts or for alleviating and treating autoimmune diseases in mammals, comprising an active ingredient selected from the group consisting of heparin and an effective chemically modified derivative thereof, wherein the dosage administered is of the order of 0.014 mg to 0.14 mg/kg of patient body weight per day, in particular 0.030 mg to 0.055 mg/kg/day.

Another embodiment of the invention is a method for preventing or delaying allograft rejection comprising administering to a human patient subject to said rejection an effective amount of heparin or of an effective chemically modified derivative thereof in a daily dosage ranging from about 0.014 mg to about 0.14 mg per kg of patient body weight, particularly 0.030 mg to 0.055 mg/kg/day.

In a further embodiment, the invention relates to a method for alleviating and treating an autoimmune disease comprising administering to a human patient suffering from such disease an effective amount of heparin or of an effective chemically modified heparin derivative in a daily dosage ranging from about 0.014 mg to about 0.14 mg per kg of patient body weight. Preferably, the disease is arthritis and the dosage is 3 mg/adult patient/day.

Left: Low dose heparin inhibits adoptively transferred DTH.

I-LNC were obtained from OX sensitized mice (groups A–C) and naive LNC from unsensitized mice (group D). The LNC were transferred intravenously to naive recipients that were treated (groups B–C) or untreated (groups A,D) with heparin (5 µg or 20 µg) injected 18 h and 1 h prior to cell transfer and 20 h after cell transfer. DTH ear swelling was elicited by OX at the time of cell transfer and measured 24 h later.

Right: Heparin inhibits cell migration to DTH challenge site. The experiment was done as described in FIG. 6 (left), except that I-LNC were radiolabeled with $^{51}$Cr prior to cell transfer into naive recipient mice. The accumulation of I-LNC in the OX challenged ears is indicated as the $^{51}$Cr (cpm/ear).

Figure 7:
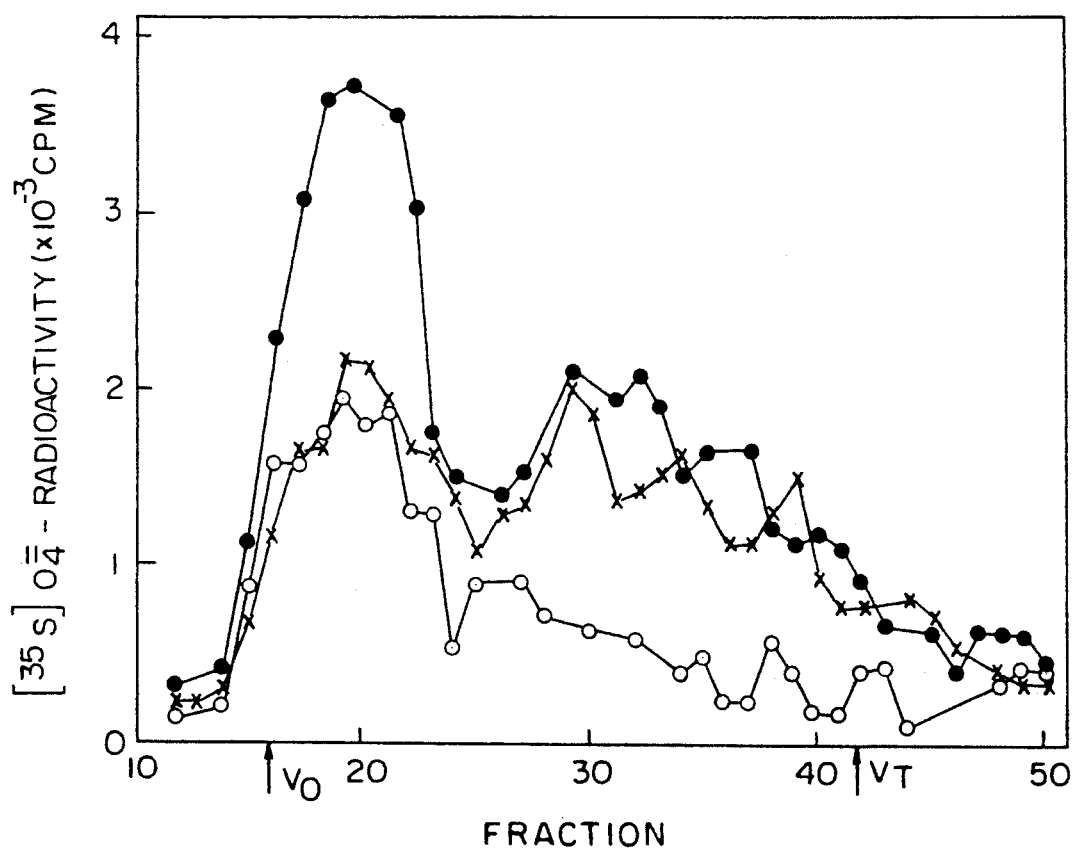

FIG. 7. Heparin inhibits heparanase in vivo

Mice were immunized with OX on days 0 and 5. Some of the mice were treated with heparin (5 µg or 25 µg per injection) 18 h before and 2, 10 and 20 h after the day 5 immunization with OX. On day 6, the I-LNC were removed and tested for heparanase activity by incubation for 48 h with labeled ECM. Heparan sulfate degradation products are shown for I-LNC from the following groups of mice: No heparin; 25 µg heparin X; 5 µg heparin-0. The LNC of control mice not immunized to OX had no heparanase activity (not shown).

Figure 8:
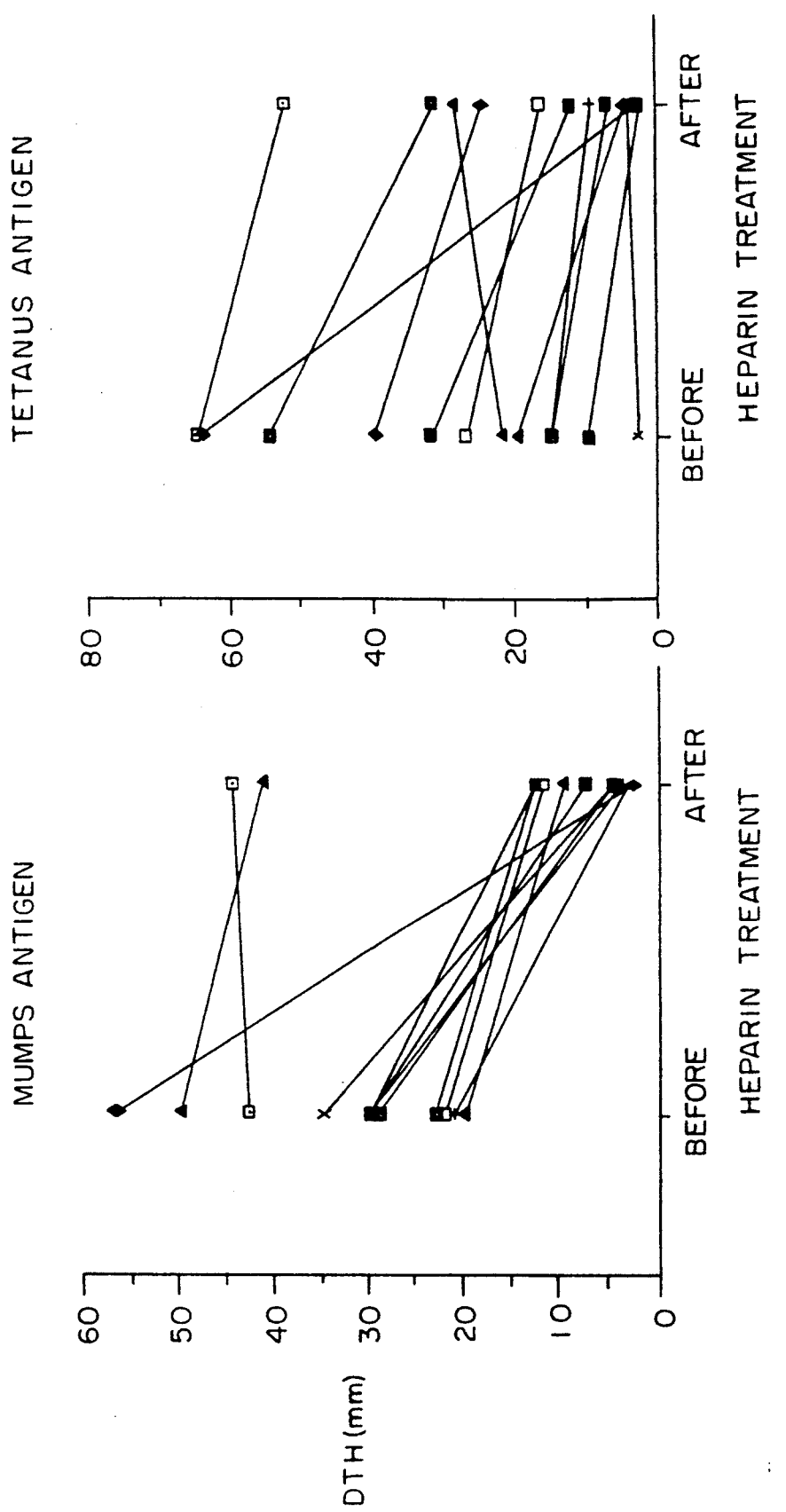

FIG. 8 Low dose heparin decreases DTH skin responses. Volunteers were treated with heparin 3 mg (500 units/day) for 10 days. Skin tests with mumps and tetanus were performed before and on the eighth day of treatment and the erythema was measured 48 h later. The response of each individual to the two antigens is designated by the same symbol.

FIG. 9. The effect of various doses of heparin on the DTH skin responses.

The effects of repeated courses of heparin treatment with either 3 mg (500 units)/day or 45 mg (7500 units)/day on the DTH skin responses (erythema) to mumps were measured in a single volunteer. Each heparin course lasted for 10 days and the skin tests were performed before, on the eighth day of treatment (during) and two months after the course of heparin treatment (after).

DETAILED DESCRIPTION OF THE INVENTION

According to the invention, there are provided pharmaceutical compositions for delaying or preventing the rejection of allografts or for alleviating and treating autoimmune diseases in mammals, comprising an active ingredient selected from the group consisting of heparin and an effective chemically modified derivative thereof, wherein the dosage administered is of the order of 0.014 mg to 0.14 mg/kg of patient body weight per day.

The heparin used in the invention, herein designated "intact heparin", is any of the commercially available heparins, examples of which are given in Table 5. The chemically modified heparins to be used in the present invention are the derivatives that inhibit T lymphocyte heparanase activity and are shown to be as effective as heparin in treating autoimmune diseases in humans. Examples of those derivatives are N-desulfated, N-acetylated heparin and O-desulfated, N-acetylated heparin.

The dosage to be used in the present invention to achieve the desired results, i.e., delay or prevention of allograft rejection and treatment of autoimmune diseases in human patients is of the order of 0.014 mg to 0.14 mg/kg of patient body weight per day, preferably from 0.030 mg to 0.055 mg/kg per day. For an adult patient weighing 70 kg, the daily dosage would be from about 1 to about 10 mg, particularly from about 2.1 to about 3.85 mg. In a preferred embodiment, the daily dosage is 3 mg for an adult patient.

These dosages correspond to from about 160 units to about 1600 units, preferably 500 units per patient per day. These are subanticoagulant doses of the order of about 0.5 to about 5 per cent of the anticoagulant effective dosage of intact heparin. The chemically modified heparins lack substantial anticoagulant activity and will be used at the same dosage as heparin or at higher dosages.

Among the autoimmune diseases that can be treated with the compositions of the invention is arthritis, in particular rheumatoid arthritis.

The compositions of the invention will be administered preferably subcutaneously. Any carrier or excipient known in the art for the administration of heparin may be used according to the invention, but the water solutions are preferred.

The following experiments were performed in animals with intact heparin or chemically modified derivatives thereof.

In order to test whether heparin or chemically modified heparins administered to experimental animals might be used to treat autoimmune diseases or to prevent graft rejection, the following experiments were carried out.

1. N-desulfated, N-acetylated modified heparin, or a low dose of intact heparin has no anti-coagulant effect in rats. Table 2 shows that intact heparin at a dose of 2 mg per rat daily (10 mg/kg) caused an increase in the prothrombin time of recipient rats. In contrast, a dose of intact heparin of 0.02 mg (0.1 mg/kg) or 2 mg of N-desulfated, N-acetylated heparin (10 mg/kg) caused no anti-coagulant effect. Thus, the potential dangers of hemorrhage attendant upon the administration of 10 mg/kg of intact heparin could be avoided by using intact heparin at a low dose (0.1 mg/kg) or a chemically modified heparin devoid of anti-coagulant activity.

2. Modified or low dose heparin inhibits skin allograft rejection.

Figure 1:
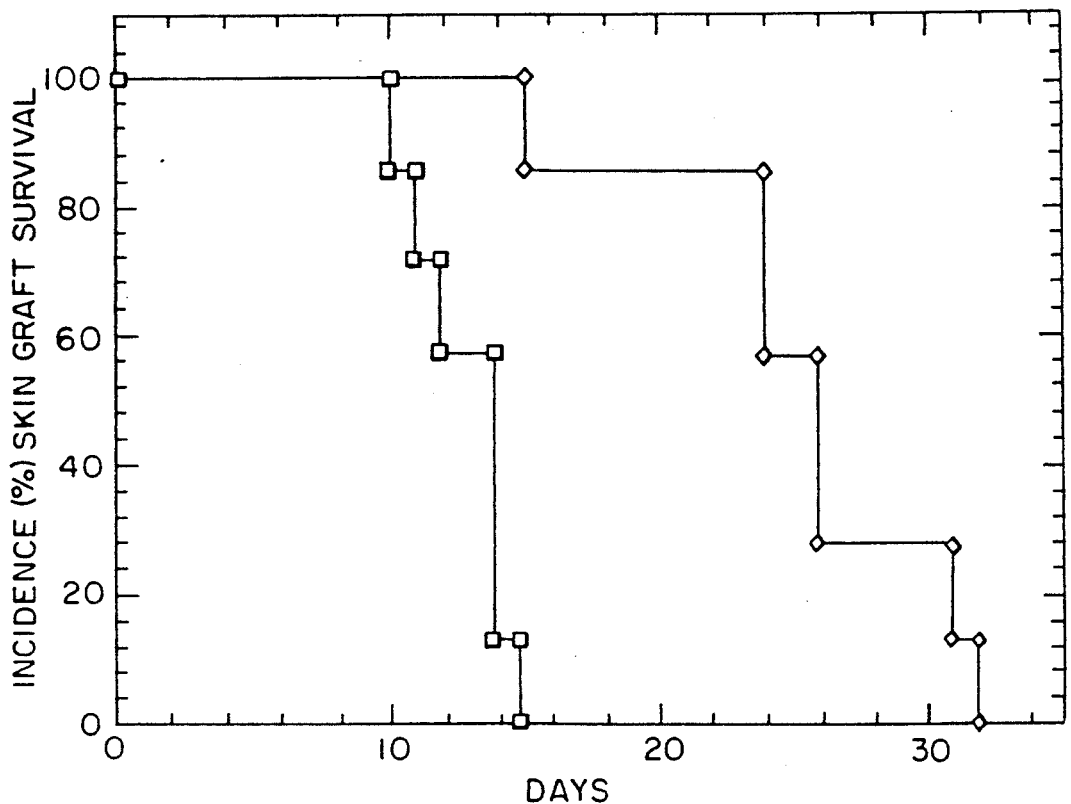
FIG. 1. Treatment with heparin (0.05 mg/kg) prevents rejection of skin allografts. Mice of hybrid strain (BALB/c×C57BL/6)F1 were grafted with skin from allogeneic SJL/J mice. The mice (20 per group) were treated daily with subcutaneous injections of saline (squares) or with heparin ("Leo", 0.05 mg/kg; diamonds) and scored for skin graft survival. Median survival for the control group was 10 days while that for the heparin treated group was 24 days.
Figure 2:
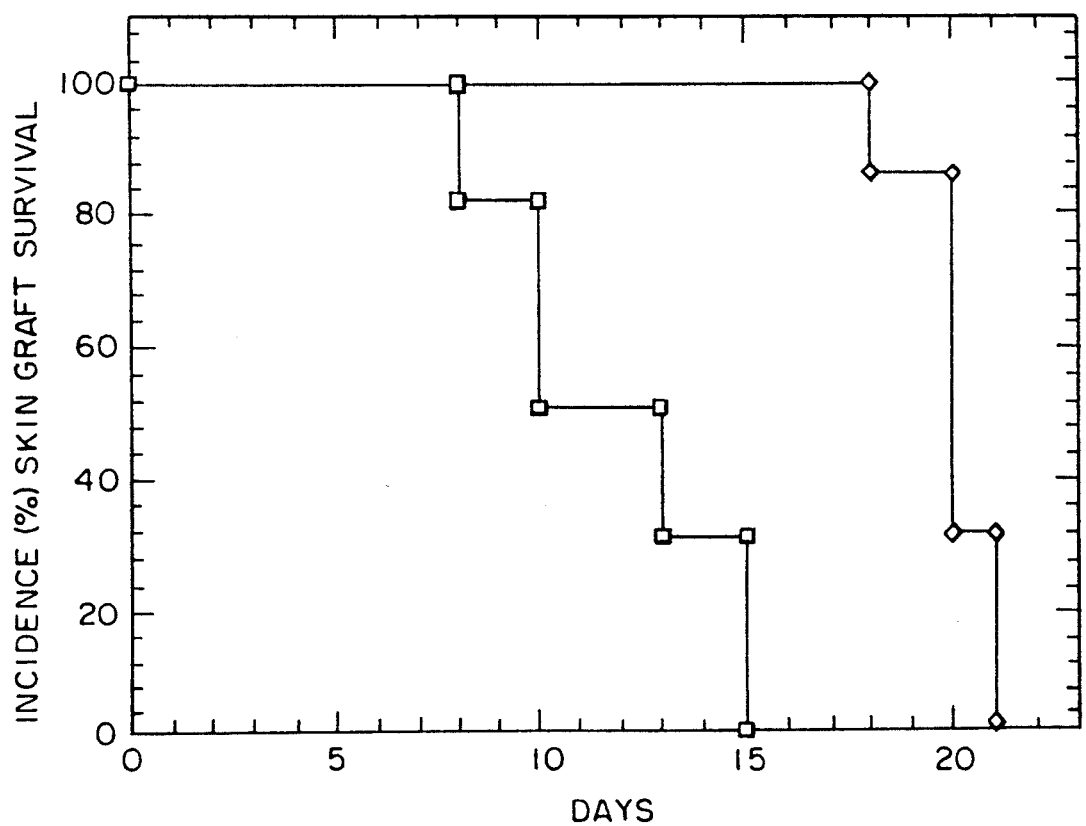
FIG. 2. Treatment with N-desulfated, N-acetylated heparin (10 mg/kg) prevents rejection of skin allografts. Mice were grafted as described for FIG. 1 and treated daily with saline (squares) or N-desulfated, N-acetylated heparin (10 mg/kg; diamonds). The median survival of the skin allograft in the control group was 10 days while that in the treated group was 20 days.

FIG. 1 shows the survival of SJL/J skin grafts on (BALB/cxC57BL/6)F1 mice. The median survival time of the skin grafts on control mice treated with saline was 14 days while that on mice treated with 0.05 mg/kg daily of heparin was 26 days with maximal survival to 32 days. FIG. 2 shows that treatment with 10 mg/kg daily of N-desulfated, N-acetylated acetylated heparin increased the median survival of the allogeneic skin grafts from 10 to 20 days.

These results indicate that a low, sub-anti-coagulant dose of heparin or a modified, non-anti-coagulant heparin can significantly increase the survival time of allogeneic skin grafts on mice.

3. Modified or low dose heparin inhibits ability of anti-BP T lymphocytes to produce experimental autoimmune encephalomyelitis (EAE).

Figure 3:
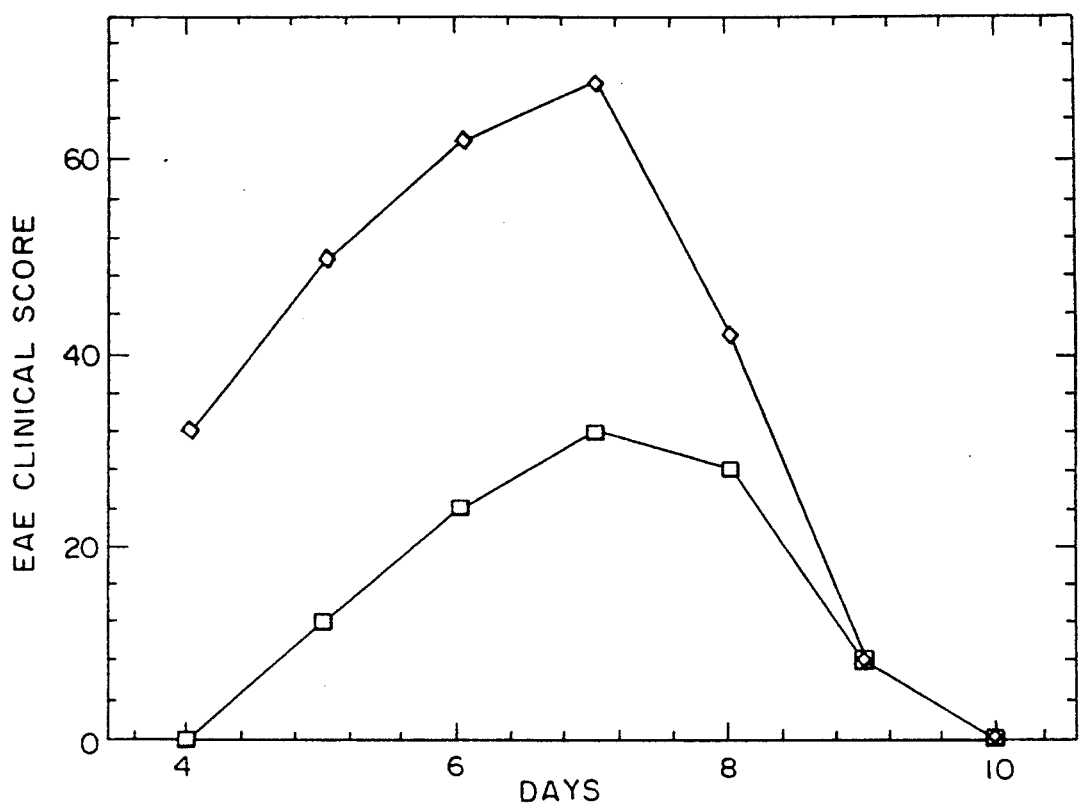
FIG. 3. Treatment with heparin (0.1 mg/kg) inhibits EAE produced by autoimmune T lymphocytes. Beginning 1 day before inoculation with the T lymphocytes, the rats were injected daily with 0.02 mg of heparin subcutaneously (0.1 mg/kg; squares). Control rats were injected with saline (diamonds), EAE clinical score was estimated as tail weakness $-25$; paralysis of hind limbs $-50$; paralysis of all 4 limbs $-75$; moribund state $-100$.

EAE is an experimental autoimmune disease with some features reminiscent of multiple sclerosis in humans. The disease is caused by T lymphocytes immunized to the basic protein (BP) of the central nervous system myelin. To test the effect of heparins on the ability of T lymphocytes to cause autoimmune disease, we used T lymphocytes sensitized against BP, either as T cell lines (Cohen, I. R. Experimental autoimmune encephalomyelitis: Pathogenesis and prevention. In: Immunoregulatory Processes in Multiple Sclerosis and Experimental Allergic Encephalomyelitis. A. A. Vandenbark and J. C. M. Raus, eds. Elsevier Biomedical Res. Amsterdam. 7:91–125 (1985)) or as populations of lymph node cells from BP immunized rats. Table 3 shows that a sub-anti-coagulant dose of intact heparin (0.1 mg/kg/day) or a dose of modified heparin (N-desulfated, N-acetylated) devoid of anti-coagulant activity (10 mg/kg/day) was able to inhibit markedly the severity of EAE produced by the anti-BP T lymphocytes. FIG. 3 shows graphically the inhibition of EAE produced by treating rats with heparin (0.02 mg/rat/day; 0.1 mg/kg).

4. Modified or low dose heparin inhibits adjuvant arthritis.

Adjuvant arthritis is an experimental disease inducible in some strains of rats by immunizing them to antigens of *Mycobacterium tuberculosis* (Pearson, C. M. Development of arthritis, periarthritis and periostitis in rats given adjuvant. Proc. Soc. Exp. Biol. Med. 91:91 (1956)). The disease is though to be a model of rheumatoid arthritis in humans (Pearson, C. M. Experimental models in rheumatoid disease. Arthritis Rheum. 7:80 (1964)). The arthritis appears to be caused by T lymphocytes that recognize an antigen of *M. tuberculosis* that is cross-reactive with cartilage (Cohen, I. R., J. Holoshitz, W. Van Eden, A. Frenkel. T lymphocytes illuminate pathogenesis and effect therapy of experimental arthritis. Arthritis Rheum. 28:841 (1985)).

Figure 4:
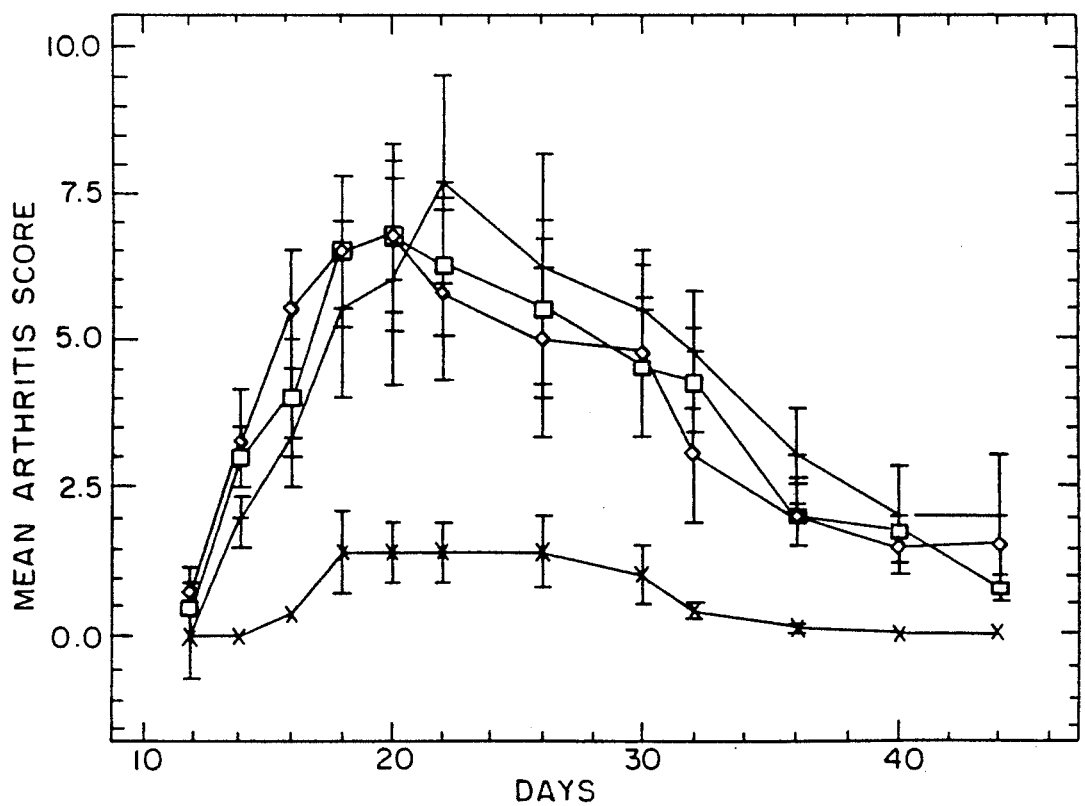
FIG. 4. Treatment of adjuvant arthritis using modified heparin (N-desulfated, N-acetylated) at various doses. Rats were immunized to induce adjuvant arthritis as described in the legend to Table 4. On day 9 the rats were inoculated subcutaneously once daily with N-desulfated, N-acetylated heparin at doses of 0 mg ($\Diamond$), 0.001 mg (—), 0.02 mg (x) or 0.04 mg ($\square$). The dose of 0.02 mg caused a significant inhibition of arthritis.

Table 4 shows that sub-anti-coagulant doses of heparin markedly inhibited adjuvant arthritis. A dose of heparin of 0.001 mg daily had a marginal effect on arthritis. Doses of 0.005 and 0.01 mg were more effective while a dose of 0.02 mg was maximally effective in inhibiting arthritis. However, the higher dose of 0.04 mg had no inhibitory effect. Thus the dose-response characteristics of treatment were very sharp; doubling the most effective dose led to total loss of activity. The sharpness of the dose response curve makes the beneficial effect of heparin on autoimmunity and graft rejection easy to miss and probably accounts for the oversight of other investigators in making our observation. Modified heparins such as N-desulfated, N-acetylated heparin also showed a similarly sharp dose-response curve with a maximum effect at 0.02 mg per rat (0.1 mg/kg). A higher dose (0.04 mg) was ineffective (FIG. 4).

Figure 5:
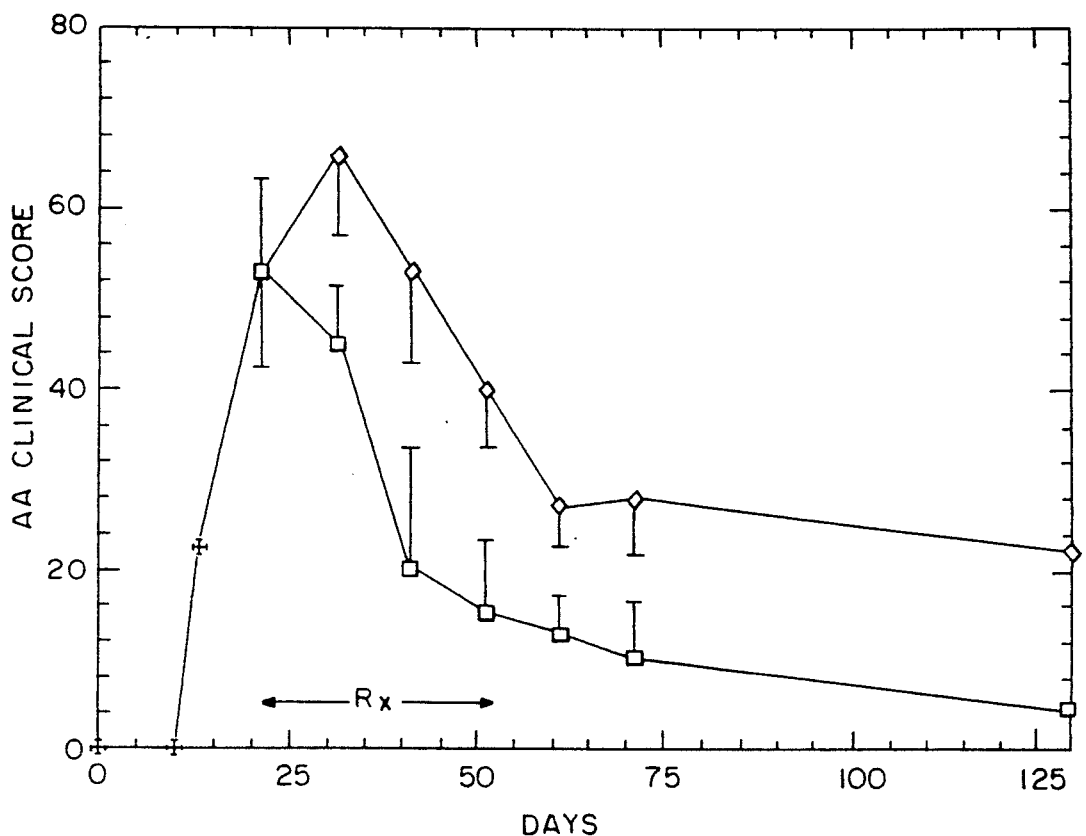
FIG. 5. Treatment with N-desulfated, N-acetylated heparin (0.1 mg/kg) induces remission of established adjuvant arthritis (AA). Twenty Lewis rats were inoculated with Mycobacteria tuberculosis to induce AA (legend to Table 4). Clinical arthritis was scored on a scale of 0 (no arthritis) to 100 (marked swelling, tenderness and redness of all 4 paws). On day 21, when all the rats were suffering from marked arthritis, 10 were inoculated subcutaneously with saline (diamonds) and 10 were treated with N-desulfated, N-acetylated heparin (0.1 mg/kg) until day 51.

FIG. 5 illustrates that modified heparin (N-desulfated, N-acetylated) at a dose of 0.1 mg/kg/day given from day 21 to 51 produced early remission of established adjuvant arthritis. Thus, treatment was effective even when the arthritis was already clinically severe. Histologic examination of the joints showed severe signs of inflammation in the control rats and healthy joints in the treated rats.

Table 5 tabulates the sources of commercially available heparin that were tested for their ability to produce long term inhibition (at day 60) of adjuvant arthritis subsequent to daily subcutaneous treatment for 5 days beginning on day 8 after induction of arthritis. Heparin obtained from 3 of 4 sources were very effective while one source was only partially effective (Organon). Thus, a variety of sources can be used to obtain active material.

Table 6 illustrates the various modified heparins that were tested for their ability to produce long term inhibition of adjuvant arthritis at day 60 as described above. Total desulfated and N-desulfated heparins were not effective in treating arthritis. However, N-desulfated, N-acetylated and O-desulfated, N-acetylated heparins were as effective as was native heparin. As demonstrated in Table 2, the modified heparins had little anticoagulant activity. Thus inhibition of undesirable immunological reactions can be achieved with various preparations of heparin devoid of the danger of anticoagulant activity.

5. Inhibition of Delayed Type Hypersensitivity (DTH) Type Skin Reactions a. Assay system:

Mice were sensitized to 4-ethoxymethylene-2-phenyl oxazolone (OX) by painting their skins twice at 5 day intervals with about 0.1 ml of 3% OX in a vehicle of 4:1 acetone:olive oil (by volume). Their immunized draining lymph node cells (I-LNC) were then transfered ($5 \times 10^7$) to recipient mice intravenously. The ability of the I-LNC to reach the site of antigen and produce a DTH reaction was assayed by challenging the recipient mice 1 hr after I-LNC transfer with 0.02 ml of 0.5% OX painted on the ear. DTH was ascertained by measuring the thickness of the ears 24 hrs later with an engineers micrometer.

The ability of the transfered I-LNC to reach the ears was tested by labeling the I-LNC before transfer with radioactive $^{51}Cr$ ($10^7$ cells/ml incubated with 0.1 mCi $^{51}Cr$ sodium chromate and washed) and measuring the amount cpm reaching the ears at the time of DTH.

b. Low dose heparin inhibits migration to site of DTH.

Figure 6:
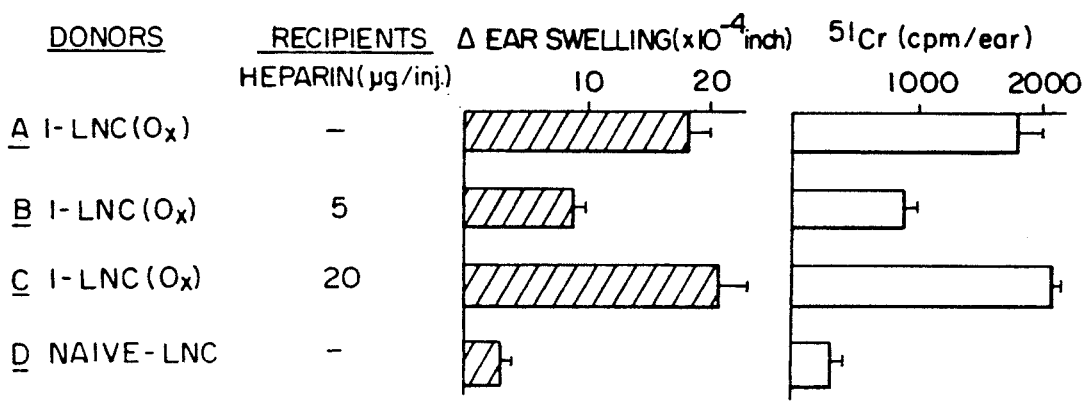
FIG. 6.

FIG. 6 shows that a dose of 5 μg daily of heparin prevents the I-LNC both from reaching the ear (decreased cpm) and from producing a DTH reaction (decreased ear swelling). A higher dose of heparin (20 μg daily) did not inhibit either I-LNC migration to the ears or DTH reactivity.

c. Modified heparin inhibits entry into, and exit from, blood vessels of activated T lymphocytes.

To test the effect of modified heparin on T lymphocyte traffic, we labelled the lymphocytes with $^{51}Cr$ and measured the uptake of the labeled lymphocytes from a subcutaneous site and their persistence in the blood. We found that the labeled lymphocytes persisted in the site of injection into the tail of rats or mice for 5–6 days in treated animals (N-desulfated, N-acetylated heparin; 0.05 mg/kg), while the labeled lymphocytes migrated from the site of injection within 1–2 days in control animals.

Furthermore, treatment with the modified heparin led to persistence of labeled lymphocytes in the blood for 4–5 days, while the untreated rats or mice cleared the labeled lymphocytes from the blood in 1 day. Thus, treatment with modified heparin inhibited the ability of T lymphocytes to enter the blood vessels, and once in the blood vessels, prevented the T lymphocytes from exiting. This can be attributed to inhibition of the heparanase enzyme activity needed to penetrate the extracellular matrix of the vessel wall.

d. Low dose heparin abrogates expression of heparanase in I-LNC

The above results indicated that treatment with the low-dose (5 μg) of heparin suppressed the ability of DTH mediating I-LNC to enter blood vessels and to accumulate at the site of antigen deposit. To learn if these effects were associated with inhibition of endogenous heparanase, we treated mice with high (25 μg) or low (5 μg) doses of heparin, sensitized them to OX and tested their I-LNC for heparanase activity in vitro. Figure shows that the I-LNC of mice treated with the low-dose (5 μg) of heparin lacked heparanase activity. In contrast, the mice treated with the high (25 μg) dose of heparin had heparanase activity that was similar to that of untreated control mice. Thus, treatment with 5 μg of heparin in vivo caused a substantial decrease of enzyme activity in sensitized lymphocytes.

e. Low-dose heparin does not abrogate an in situ DTH reaction

If inhibition of heparanase and heparanase-dependent traffic is the major mechanism by which low dose heparin suppresses DTH, then one might be able to bypass the inhibition of DTH by bypassing the need for vascular traffic of sensitized T lymphocytes. Accordingly we treated recipient mice with an inhibitory dose (5 μg) of heparin, and then injected the donor I-LNC directly into the ears, rather than intravenously. Table 7 illustrates that putting the sensitized lymphocytes in situ bypassed the inhibitory effect on the DTH of 5 μg of heparin. Thus low dose heparin treatment appeared to inhibit DTH only when the DTH-mediat lymphocytes had to make their way to the site of the antigen by way of the circulation.

The conclusions of these studies are as follows:

1. A low dose of heparin inhibits DTH reaction, as it does graft rejection and autoimmune diseases in experimental animals.

2. These effects are associated with a decrease in T lymphocyte heparanase and T lymphocyte migration to the site of the antigen.

The results indicate that an inhibitor of heparanase, such as heparin or N-desulfated, N-acetylated heparin, can be used to prevent autoimmunity and allograft rejection. The effective dose of heparin of the order of 0.1 mg/kg, is about 1% or less of that used to produce an anti-coagulant effect (10 mg/kg) and therefore prevention of undesirable immune reactions can be separated from anti-coagulation, N-desulfated, N-acetylated and O-desulfated, N-acetylated heparins are intrinsically devoid of anti-coagulant activity and can be used at a higher dose of the order of 10 mg/kg although lower doses (0.1 mg/kg) of these materials are more effective in preventing unwanted immune reactions. This dose is critical because, as shown in Table 4, 0.02 mg/rat (0.1 mg/kg) can be optimal in inhibiting disease while a higher dose, 0.04 mg/rat (0.2 mg/kg) can be ineffective. The same sensitivity of effect to dose was also observed with the modified heparins such as N-desulfated, N-acetylated heparin.

The results show that commercial heparin or certain chemically modified heparins at surprisingly low doses have a specific inhibitory effect on T lymphocyte heparanase expression and cell traffic, thus providing a rationale and guide to the use of heparinoids as immunomodulators. A key observation was that these heparanase inhibitors were less effective at higher doses than they were at lower doses both in vivo and in vitro. As shown in the examples, we were able to inhibit the experimental autoimmune diseases EAE and AA in rats, and allograft rejection in mice by using suitable doses of heparins.

6. Treatment of Humans

The expression of T cell heparanase was found to be inhibited by treatment of experimental animals with low doses, but not by high doses of heparin. Such treatment was found to inhibit T cell traffic to the site of the specific antigen and decrease the delayed type hypersensitivity (DTH) skin response in immunized mice and rats.

Moreover, low doses of heparin inhibited the induction of adjuvant arthritis and experimental allergic encephalomyelitis in rats, postponed the rejection of skin allografts in mice These findings suggest that low doses of heparin might have a therapeutic role in T cell mediated autoimmune diseases and in organ transplantation in humans. To learn whether human T cell reactions were susceptible to inhibition by low doses of heparin, we tested the effect of heparin on the DTH skin response of human volunteers. We herein show that the DTH skin response in healthy humans could be reversibly inhibited using very low doses of heparin.

METHODS

Antigens

Mumps skin test antigen was purchased from Connaught Laboratories, Inc., Swiftwater, PA and Tetanus toxoid from Rafa Laboratories, Jerusalem.

Skin Tests 0.1 ml of antigen solution was injected intradermally in the forearm. The diameters of the induration and erythema were measured 48 hours later.

Heparin Treatment

Healthy volunteers, informed and consenting medical students and members of the medical staff, had a mean age of 30 years (range 22-39). Each was treated with a single daily subcutaneous injection of either heparin 3 mg (500 units)/day, (0.1 ml 5000 units/ml) or saline for ten days. Skin tests with mumps and tetanus were performed before treatment and on the eighth day of treatment.

One volunteer received, in addition, a course of higher doses of heparin: 45 mg (7500 units) per day for 10 days.

RESULTS

Low Doses of Heparin Decrease the DTH Response

To study the effect of low dose heparin on cell mediated immunity, the local response to intradermal injection of mumps or tetanus toxoid antigens was measured before and during treatment with heparin in 12 volunteers. The dose of 3 mg (500 units) daily was derived by extrapolation from the optimal doses in mice and rats. As can be seen in FIG. 8, the DTH response to mumps and tetanus decreased significantly in most of the volunteers (11/12 and 10/12, respectively). The mean diameter of erythema to mumps decreased from 32.5 mm to 13.6 mm and to tetanus toxoid from 30.7 to 16.8 mm. The extent of induration decreased similarly. No significant change in the DTH response was observed in volunteers who were treated for 10 days with saline (not shown).

A single volunteer (investigator Y.N.) was treated on three different occasions with two different doses of heparin to learn whether the inhibition of DTH was reversible and whether in humans as in animals, a low dose was more effective than a high dose of heparin.

As shown in FIG. 9, the effect of 3 mg (500 units) of heparin on the DTH response was transient and the skin test response returned to the original magnitude two months after termination of treatment. Moreover, a course of 45 mg (7500 units) daily for 10 days did not have a significant inhibitory effect on the DTH response.

These results indicate that daily treatment of healthy humans with 3 mg (500 units) of heparin inhibits the DTH skin response to T cell related antigens. A higher dose, 45 mg (7500 units) daily, was tested on one person and showed no inhibitory effect.

As is shown in FIG. 9, the DTH response returned to its pre-treatment magnitude a few weeks after heparin treatment was stopped. This indicates that the decrease in the DTH response was not an artifact of repeated skin tests. More importantly, the inhibitory effect of heparin is transient.

The effective dose of heparin, 3 mg (500 units) per day, was computed from the optimal dose per weight in mice and rats and corrected for surface area. This dose of heparin is much less than the dose affecting the coagulation system and indeed no change in the partial thromboplastin time was observed after injection of these low doses of heparin to the human volunteers. (not shown).

How can we explain these findings? The pharmacokinetics of heparin is dose dependent.

We have shown above that the effects of heparin in mice and rats on heparanase and on the development of adjuvant arthritis is not related to its anticoagulant effect: partially desulfated derivatives of heparin with no anticoagulant activity were effective. Inhibition of heparanase is the only known effect restricted to low-dose heparin that could account for inhibition of DTH. Certainly, the inhibition of DTH by 3 mg (500 units), but not by 45 mg (7500 units) cannot be attributed to anti-coagulation. Thus, inhibition of DTH in humans as in animals may be attributed to inhibition of heparanase.

As DTH reactions to self antigens are involved in autoimmune diseases, we have begun to test low dose heparin (about 300-500 units daily) in patients with rheumatoid arthritis. Three patients with severe arthritis were treated for 1 month and all 3 were improved; they felt better subjectively and they had a decrease in their clinical disability and arthritis as assessed by their physicians.

TABLE 1

| Inhibition of heparanase activity | |
|---|---|
| Test inhibitor | Inhibition of degradation of heparan sulfate by heparanase |
| Heparin: intact | yes |
| Heparin: totally desulfated | no |
| Heparin N-desulfated, N-acetylated | yes |

Heparanase activity was induced into the extracellular medium bathing activated T lymphocytes and tested by incubating the medium with extracellular matrix whose heparan sulfate was labeled with $^{35}S$ as described (Naparstek, Y., Cohen, I. R., Fuks, Z. and I. Vlodavsky. Activated T lymphocytes produce a matrix-degrading heparan sulphate endoglycosidase. Nature 310:241 (1984)). Inhibition of heparanase activity was tested by adding various concentrations of heparin or modified heparins to the reaction mixture and measuring the effect on degradation of the labeled heparin-sulfate as described (Naparstek, Y., Cohen, I. R., Fuks, Z. and I. Vlodavsky.

Activated T lymphocytes produce a matrix-degrading heparan sulphate endoglycosidase, Nature 310:241 (1984)). Totally desulfated heparin and N-desulfated, N-acetylated heparin was prepared as described. (Ayotte, L., A. S. Perlin. NMR spectroscopic observations related to the function of sulfate groups in heparin. Calcium binding vs. biological activity. Carbohydrate Res. 145:267 (1986)).

TABLE 2

Effect on prothrombin time of heparins

| Injected material | Dose (mg) | Pro-thrombin time (min) | Anti-coagulation |
|---|---|---|---|
| None | 0 | 19 | — |
| Heparin | 20 | 25 | yes |
| Heparin | 0.2 | 17 | no |
| Heparin N-desulfated, N-acetylated | 20 | 19 | no |

Lewis rats, 10 weeks old weighing 250 gm, were injected subcutaneously with the indicated dose of heparin once daily for 2 days. The prothrombin time was then tested as described in the "Pathromtin Kit-OTX8" (Hoechst-Behring, Marburg, FRG).

TABLE 3

Inhibition of experimental autoimmune encephalomyelitis (EAE) by treatment with a sub-anti-coagulant dose of intact heparin or with modified heparin (N-desulfated, N-acetylated).

| Agent | Dose (mg/kg) | Mediation of EAE | % incidence | Day of onset | Duration (days) | Clinical score |
|---|---|---|---|---|---|---|
| A. None | — | T cell line | 100 | 5.2 | 4.2 | 2.4 |
| Modified Heparin | 10 | | 50 | 6.4 | 1.8 | 0.8 |
| B. None | — | T cell line | 100 | 5.0 | 5.5 | 3.0 |
| Heparin | 0.1 | | 20 | 6.5 | 3.6 | 1.0 |
| C. None | — | Primed lymph node | 80 | 4.5 | 5.8 | 2.3 |
| Modified Heparin | 10 | | 0 | — | — | — |
| D. None | — | Primed lymph node | 100 | 4.0 | 5.3 | 3.0 |
| Heparin | 0.1 | | 75 | 6.3 | 4.0 | 1.5 |

EAE was produced by inoculating Lewis rats with a T cell line of anti-BP T lymphocytes ($10^6$ cells) with anti-BP primed lymph node cells ($10^7$ cells) intravenously (Cohen, I. R. Experimental autoimmune encephalomyelitis: Pathogenesis and prevention. In: Immunoregulatory Processes in Multiple Sclerosis and Experimental Allergic Encephalomyelitis. A. A. Vandenbark and J. C. M. Raus, eds. Elsevier Biomedical Res. Amsterdam. 7:91-125 (1985)) One day before inoculation and daily for 10 days, the rats received either saline or the heparins. The rats were observed for development of paralysis graded 1 for tail weakness; 2 for paralysis of hind limbs; 3 for paralysis of hind and forelimbs; and 4 for moribund state

TABLE 4

Treatment of adjuvant arthritis by sub-anti-coagulant doses of heparin.

| Heparin dose (mg) | Adjuvant Arthritis | |
|---|---|---|
| | Duration (days) | Maximum clinical score |
| 0 | >20 | 10 |
| 0.04 | >20 | 10 |
| 0.02 | 8 | 2 |
| 0.01 | 15 | 5 |
| 0.005 | 16 | 4 |
| 0.001 | 20 | 6 |

Rats were immunized with *M. tuberculosis* (1 mg) in oil to induce adjuvant arthritis (Pearson, C. M. Development of arthritis, periarthritis and periostitis in rats given adjuvant. Proc. Soc. Exp. Biol. Med. 91:91 (1956)). On day 9 the rats were incubated subcutaneously once daily for 5 days with various doses of heparin and scored for the development of arthritis on a scale of 0–16 as described (Holoshitz, Y., Y. Naparstek, A. Ben-Nun, I.R. Cohen. Lines of T lymphocytes mediate or vaccinate against autoimmune arthritis. Science 219:56 (1983)).

TABLE 5

Sources of Heparin tested for inhibition of adjuvant arthritis.

| Heparin | Company | Arthritis Score (day 60) | Inhibition of Arthritis |
|---|---|---|---|
| Leo | Leo Pharmaceutical Ballerp, Denmark | 0 | yes |
| Sigma (bovine lung) | Sigma Chemical Co. St. Louis, MI, USA | 0 | yes |
| BDH | BDH Chemicals, Poole, England | 0 | yes |
| Thromboliquine | Organon Teknika, Boxtel, Holland | 2.5 | partial |
| Untreated | — | 5 | — |

Adjuvant arthritis was induced in Lewis rats and the rats were treated with the indicated sources of heparin as described in the legend to Table 4. The mean arthritis score determined on day 60 was used to assay the efficacy of heparin treatment.

TABLE 6

Modified heparins tested for inhibition of adjuvant arthritis.

| Heparin | Arthritis score (day 60) | Inhibition of arthritis |
|---|---|---|
| None | 6 | — |
| Intact | 0 | yes |
| N-desulfated, N-acetylated | 0 | yes |
| O-desulfated, N-acetylated | 0 | yes |
| Total desulfated | 5 | no |
| N-desulfated | 5 | no |

Adjuvant arthritis was induced in Lewis rats and the rats were treated with modified heparins as described in the legends to Tables 4 and 5. The heparins were modified as described (Ayotte, L., A. S. Perlin. NMR spectroscopic observations related to the function of sulfate groups in heparin. Calcium binding vs. biological activity. Carbohydrate Res. 145:267 (1986)).

TABLE 7

This Table illustrates that heparin does not block transfer of DTH when I-LNC are directly injected into the site of antigen challenge

| Recipients of I-LNC sensitized to OX | | |
|---|---|---|
| Heparin treatment (5 u.g) | OX Challenge | Ear swelling ($\times 10^{-4}$ inch) |
| No | Yes | 22 ± 3.4 |
| Yes | Yes | 20.4 ± 1.6 |
| No | No | 9 ± 1.0 |
| Yes | No | 8 ± 1.0 |

I-LNC were obtained from BALB/c mice sensitized to OX 5 days earlier. The I-LNC were centrifuged, resuspended in RPMI medium and injected intradermally ($3 \times 10^6$ cells/20 μ/l) into the dorsal surface of the ears of naive recipient mice. The ears were challenged with OX immediately after cell transfer. The magnitude of DTH ear swelling was determined 24 h later.

We claim:

1. A method for inhibiting heparanase activity comprising administering to a patient in need thereof an effective heparanase inhibiting amount of a composition consisting essentially of an active ingredient selected from the group consisting of heparin and an effective chemically modified derivative thereof which inhibits heparanase and a pharmaceutically acceptable carrier.

2. The method according to claim 1 wherein said heparanase activity is T-lymphocyte heparanase activity.

3. A method for preventing or delaying allograft rejection comprising administering to a human patient subject to said rejection an effective amount of a compound selected from the group consisting of heparin and effective chemically modified derivatives of heparin which inhibit heparanase in a daily dosage ranging from about 0.014 mg to about 0.14 mg per kg of patient body weight.

4. Method for alleviating and treating an autoimmune disease comprising administering to a human patient suffering from such disease an effective amount of a compound selected from the group consisting of heparin and effective chemically modified derivatives of heparin which inhibit heparanase in a daily dosage ranging from about 0.014 mg to about 0.14 mg per kg of patient body weight.

5. A method according to claim 4 wherein the autoimmune disease is arthritis comprising administering to a human patient a daily dosage of heparin of the order of from 0.030 mg to 0.055 mg per kg of body weight.

6. A method according to claim 5 wherein a daily dosage of 3 mg of heparin is administered to an adult human patient.

7. A method in accordance with claim 5, wherein said compound is selected from the group consisting of heparin; N-desulfated, N-acetylated heparin; and O-desulfated, N-acetylated heparin.

8. A method in accordance with claim 4, wherein said compound is selected from the group consisting of heparin; N-desulfated, N-acetylated heparin; and O-desulfated, N-acetylated heparin.

9. A method in accordance with claim 1, wherein said active ingredient is selected from the group consisting of heparin; N-desulfated, N-acetylated heparin; and O-desulfated, N-acetylated heparin.

* * * * *